United States Patent [19]

Curran et al.

[11] 3,976,683
[45] Aug. 24, 1976

[54] α-AMINO SUBSTITUTED THIOACETAMIDES

[75] Inventors: Adrian Charles Ward Curran; Roger Crossley, both of Reading, England

[73] Assignee: John Wyeth & Brother Limited, Taplow, England

[22] Filed: Mar. 18, 1974

[21] Appl. No.: 452,028

[30] Foreign Application Priority Data
Mar. 29, 1973  United Kingdom............... 15067/73

[52] U.S. Cl.................. 260/501.19; 260/551 S; 260/465 C; 260/501.21; 424/320
[51] Int. Cl.[2]..................................... C07C 153/063
[58] Field of Search ....... 260/551 S, 501.19, 501.21

[56] References Cited
OTHER PUBLICATIONS
CA 56: 404c, "Compounds with Spasmolytic Activity," Klosa, 1961.
CA 51: 15579h, "Spasmolytically Active Substituted p-methoxyphenylacetamides," N. V. Neder, 1957.
CA 52: 1241i, "Spasmolytics," N. V. Neder, 1956.

CA: 14164d, "Some α-dialkylaminophenylacetonitriles," Morris et al., 1961.
CA 49: 13237g, "Antispasmodics," Janssen, 1954.
*Medicinal Chemistry,* Burger, Ed., Interscience, 2nd Ed., p. 492 (1960).

*Primary Examiner*—Daniel E. Wyman
*Assistant Examiner*—Thomas A. Waltz

[57] ABSTRACT

The invention relates to thioamides of formula I

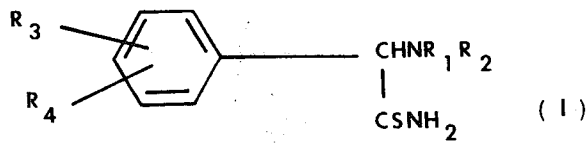

and acid addition salts thereof wherein $R_1$ and $R_2$ are selected from the group consisting of hydrogen, lower alkyl, and phenyl and $R_3$ and $R_4$ are selected from the group consisting of hydrogen and lower alkoxy, with proviso that when $R_3$ and $R_4$ are both hydrogen at least one of $R_1$ and $R_2$ is other than hydrogen.

3 Claims, No Drawings

A-AMINO SUBSTITUTED THIOACETAMIDES

The invention relates to novel thioamides, to pharmaceutical compositions containing them and to processes for preparing the novel compounds.

According to the invention there are provided thioamides of formula I

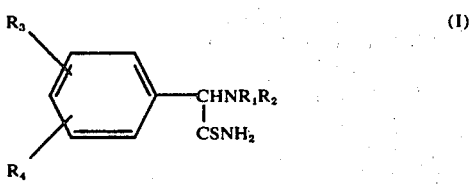

and acid addition salts thereof wherein $R_1$ and $R_2$ are selected from the group consisting of hydrogen, lower alkyl, and phenyl and $R_3$ and $R_4$ are selected from the group consisting of hydrogen and lower alkoxy, with the proviso that when $R_3$ and $R_4$ are both hydrogen at least one of $R_1$ and $R_2$ is other than hydrogen.

Examples of lower alkoxy groups for $R_3$ and $R_4$ are methoxy ethoxy and propoxy.

The phenyl group shown in formula I may be monosubstituted e.g. at the 4-position, or disubstituted, e.g. at the 3 and 4 positions.

Lower alkyl groups used as $R_1$ or $R_2$, include n-, s and t-lower alkyl groups e.g. methyl, ethyl, n-, s- and t-butyl and cycloalkyl groups e.g. cyclobutyl, cyclopentyl and cyclohexyl.

Preferably $R_1$ and $R_2$, are both hydrogen atoms.

The invention includes methods of preparing compounds of formula I.

A method of preparing compounds of formula I comprises reacting a nitrile of formula II

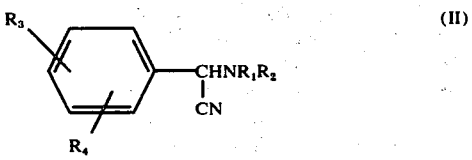

with a thioamide of formula $R_5CSNH_2$ where $R_5$ is an alkyl group e.g. a lower alkyl group of 1 to 6 carbon atoms, preferably a methyl group, in a suitable solvent e.g. dimethylformamide saturated with hydrogen chloride.

A method of preparing compounds of formula I, wherein $R^3$ and $R^4$ are both hydrogen comprises reacting a corresponding α-amino-nitrile of formula II with hydrogen sulphide in the presence of a base such as a trialkylamine e.g. triethylamine. A solvent e.g. a weakly basic solvent such as pyridine or lutidine may be used. When $R_1$ or $R_2$ is a branched chain alkyl or aralkyl group with a secondary or tertiary carbon atom attached directly to the nitrogen atom the thioamide is generally accompanied by a substantial amount of a thiol of formula $RCH_2SH$ or a disulphide of formula $RCH_2SSCH_2R$.

If $R^3$ or $R^4$ is an alkoxy group and $R_1$ or $R_2$ is a branched chain alkyl or aralkyl group as defined then no significant amount of thioamide product appears to be formed.

The amino nitriles of formula II used as starting materials in the above processes are either known compounds or novel compounds which can be prepared by known methods.

Compounds of formula I have been found to possess pharmacological activity e.g. anti-ulcer activity. The anti-ulcer activity was determined by the method of Brodie and Hanson, Gastroenterology 38 353 1960. Some compounds of formula I also display antisecretory activity in the test of H. Shay, D. Sun and M. Greenstein, Gastroenterology 1954, 26, 906–13.

α-Isopropylamino-α-phenyl thioacetamide and α-dimethylamino-α(3,4-dimethoxyphenyl) thioacetamide show particularly good anti-ulcer activity.

The invention also includes pharmaceutical compositions comprising a compound of formula I and a pharmaceutical carrier.

For the pharmaceutical carrier any suitable carrier known in the art can be used to prepare the pharmaceutical compositions. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet-disintegrating agents; it can also be an encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10 to 80% of the active ingredient. Suitable solid carriers are magnesium carbonate, magnesium stearate, talc, sugar, lactose, pectin, dextrin, starch, gelatin, tragacanth, methyl cellulose, sodium carboxymethyl cellulose, a low melting wax, and cocoa butter. The term "composition" is intended to include the formulation of an active ingredient with encapsulating material as carrier to give a capsule in which the active ingredient (with or without other carriers) is surrounded by carrier, which is thus in association with it. Similarly cachets are included.

Sterile liquid form compositions include sterile solutions, suspensions, emulsions, syrups and elixirs. The active ingredient can be dissolved or suspended in a pharmaceutically acceptable sterile liquid carrier, such as sterile water, sterile organic solvent or a mixture of both. The active ingredient can often be dissolved in a suitable organic solvent, for instance aqueous propylene glycol or polyethylene glycol solutions. Aqueous propylene glycol containing from 10 to 75% of the glycol by weight is generally suitable. In other instances compositions can be made by dispersing the finely-divided active ingredient in aqueous starch or sodium carboxymethyl cellulose solution, or in a suitable oil, for instance arachis oil.

Preferably the pharmaceutical composition is in unit dosage form, the composition is sub-divided in unit doses containing appropriate quantities of the active ingredient; the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of compositions may be varied or adjusted from 5 mg. or less to 500 or more, according to the particular need and the activity of the active ingredient. The invention also includes the compounds in the absence of carrier where the compounds are in unit dosage form.

The anti-ulcer compositions of the invention will be administered orally in either liquid or solid composition form. These compositions may include one or more antacid ingredients e.g. aluminium hydroxide, magnesium hydroxide or bismuth carbonate, aluminium glycinate, calcium carbonate, magnesium trisilicate, sodium bicarbonate or the alumina gel described in British Specification No. 1,284,394.

In the compounds of formula I the carbon atom marked with an asterisk is asymmetric.

Consequently the compounds can exist in optically active $d$ and $l$ forms. These optically active forms and the racemates are included in the invention. The optically active forms may be separated by standard resolution techniques e.g. by formation of an acid addition salt with an optically active acid.

The following examples illustrate the invention:

EXAMPLE 1

α-Methylamino-α-(3,4-dimethoxybenzyl)thioacetamide

α-Methylamino-α-(3,4-dimethoxybenzyl)acetonitrile was prepared from veratraldehyde according to the method of J. Klosa (*J. Prakt. Chem.*, 1961, 12, 258-63) and converted to the hydrochloride by passing dry HCl gas into an ethereal solution and collecting the precipitated hydrochloride salt. (65% yield) m.p. 152°–4° (lit. 153°–4°) [Found: C, 54.19; H, 6.22; N, 11.04%. $C_{11}H_{14}N_2O_2$ HCl requires: C, 54.44; H, 6.23; N, 11.54%].

The above aminonitrile (5 gm) was dissolved in a mixture of pyridine (20 ml.) and triethylamine (6 ml) and the solution treated with hydrogen sulphide at room temperature for 2 hours with stirring. The red solution was transferred to a sealed flask and allowed to stand at room temperature for 16 hours. Removal of the volatile material in vacuo gave a residual brown oil which was dissolved in ether (100 ml) and washed with water (3 × 15 ml), 2N̄ HCL(2 × 50ml) and water (2 × 50ml). The ethereal solution was dried and evaporated in vacuo to give 3,4-dimethoxybenzyldisulphide as a pale yellow solid (80% yield) which recrystallised from isopropanol as colourless needles m.p. 83°[Found: C,59.28; H, 6.14%. $C_{18}H_{22}S_2$ requires C, 59.99; H, 6.05%].

The acid extracts were combined and the pH adjusted to 12.0 with 2N̄ NaOH and extracted into ether (3 × 50 ml.). The combined ethereal extracts were washed with brine (2 × 50 ml.), dried and evaporated in vacuo to give α-methylamino-α-(3,4-dimethoxybenzyl)thioacetamide (20% yield) which was isolated as a pale yellow solid and recrystallised from ethanol as creamy needles m.p. 204° (dec.) [Found: C,55.27; H, 6.68; N,11,64%. $C_{11}H_{16}N_2SO_2$ requires: C, 54.98; H, 6.71; N, 11.66%].

EXAMPLE 2

α-Isopropylamino-α-phenylthioacetamide.

α-Isopropylamino-α-phenylacetonitrile was prepared from benzaldehyde according to the method of G. Morris (*J.O.C.*1961, 26, 4741) and was treated with $H_2S$ as described in Example 1 to give benzylmercaptan as a colourless oil (56%) characterised as the 2,4-dinitrophenyl derivative m.p. 130° (*Vogel-Practical Org. Chem.* m.p. 130°). The benzyl mercaptan was slowly oxidised in air to benzyldisulphide m.p. 71.3° [Found: C,68.74; H,5.92%. $C_{14}H_{14}S_2$ requires: C,68.25; H, 5.73%] (lit mpt.71°, Heilbron, *Dictionary of Org. Compounds* p.904 Hinsberg. Ber. 1912, 45, 2339). In addition, the acid-base extraction work up procedure described in Example 1 gave α-isopropylamino-α-phenylthioacetamide as colourless needles (36% yield) m.p. 98.6° [Found: C,63.92; H,7.93; N,13.43%. $C_{11}H_{16}N_2S$ requires: C, 63.39; H,7.74; N,13.48%].

EXAMPLE 3

α-Anilino-α-(3,4-dimethoxyphenyl)thioacetamide

α-Anilino-α-(3,4-dimethoxyphenyl)acetonitrile was prepared from veratraldehyde according to the method of G. Morris (*J.O.C.*1961, 26, 4741) and isolated as colourless needles mlp. 147° [Found: C,63.71; H,6.07; N,9.01%. $C_{16}H_{16}N_2O_2$ requires C,63.55; H,6.00; N,9.26%]

α-Anilino-α-(3,4-dimethoxyphenyl)acetonitrile (5 gm) was suspended in a mixture of pyridine (20 ml.) and triethylamine 6 ml) and the solution treated with $H_2S$ for 2 hours and then allowed to stand in a stoppered flask for 16 hours. The volatile material was removed and the residual solid was shaken with 2N̄ HCl (100 ml.) and ether (75 ml.) and the ethereal layer separated. This extraction process was repeated three times. The combined ethereal extracts were washed with water, dried and evaporated to give no product (i.e. no mercaptan). The acidic washings were made basic with saturated $Na_2CO_3$ and the resultant solid filtered, dried and recrystallised from isopropanol to give the title compound as colourless needles (5.1 gm., 90%) m.p. 171° (dec.) [Found: C,63.71; H,6.07; N,9.01%. $C_{16}H_{18}N_2SO_2$ requires: C,63.55; H,6.00; N9.26%].

EXAMPLE 4

α-Dimethylamino-α(3,4-dimethoxyphenyl)thioacetamide

α-Dimethylamino-α-(3,4-dimethoxyphenyl)acetonitrile was prepared from veratraldehyde, according to the method of G. Morris (*J.O.C.* 1961, 26, 4741), and isolated as colourless needles from isopropanol m.p. 95°. α-Dimethylamino-α-(3,4-dimethoxyphenyl)acetonitrile was dissolved in a mixture of pyridine (20 ml.) and triethylamine (6 ml.) and the solution treated with $H_2S$ for 2 hours and then allowed to stand at room temperature in a stoppered flask for 16 hours. The volatile material was removed in vacuo and the residual oil dissolved in ether (200ml.). The ethereal solution was washed with water (2 × 50 ml.), saturated $Na_2CO_3$ (2 × 50 ml.) 2N̄ HCl (2 × 50 ml.), brine and was dried and evaporated in vacuo to give no product (i.e. no thiol). The combined acid washings were made basic with saturated $Na_2CO_3$ and extracted into chloroform (4 × 50 ml.) and then ethylacetate (2 × 50 ml.). The combined extracts were washed with brine, dried and evaporated in vacuo to give a solid residue which was recrystallised from ethyl acetate giving colourless needles (25% yield) m.p. 176° (dec.) [Found: C,57.00; H,7.23; N,10.97%. $C_{12}H_{18}N_2SO_2$ requires C,56.67; H,7.13; N,11.01%].

EXAMPLE 5

α-Dimethylamino-α-phenylthioacetamide.

α-Dimethylamino-α-phenylacetonitrile was prepared according to the general method of G. Morris (*J.O.C.*1961, 26, 4741) and isolated as the hydrochloride [Found: C,60.99; H,6.88; N,13.96%. $C_{10}H_{12}N_2.HCl$ requires: C,61.07; H,6.6; N,14.24%].

The title compound was prepared from α-dimethylamino-α-phenylacetonitrile by the general method described in Example 4 and was isolated as colourless needles from diisopropylether. (25% yield) m.p. 147°. [Found: C,61.97; H,7.22; N,14.25%. $C_{10}H_{14}N_2S$ requires: C,61.82; H,7.26; N,14.42%].

The compounds of formula I can form acid addition salts with inorganic acids e.g. hydrochloric, hydrobromic, sulphuric or nitric acids, or organic acids e.g. oxalic, fumaric, maleic or tartaric acids. These acid addition salts are included in the invention.

We claim:
1. A compound selected from the group consisting of α-isopropylamino-α-phenylthioacetamide, α-dimethylamino-α-(3,4-dimethoxyphenyl)thioacetamide, and their acid addition salts with pharmaceutically acceptable acids.
2. α-Isopropylamino-α-phenylthioacetamide.
3. α-Dimethylamino-α(3,4-dimethoxyphenyl)thioacetamide.

* * * * *